United States Patent
Gruenbacher et al.

(10) Patent No.: US 11,957,816 B2
(45) Date of Patent: Apr. 16, 2024

(54) VOLATILE COMPOSITION DISPENSER HAVING AN AIR PUMP AND A METHOD OF DELIVERING A VOLATILE COMPOSITION TO AN EVAPORATIVE SURFACE USING THE SAME

(71) Applicant: The Procter & Gamble Company, Cincinnati, OH (US)

(72) Inventors: Dana Paul Gruenbacher, Fairfield, OH (US); Stephan Gary Bush, Liberty Township, OH (US); William Paul Mahoney, III, Liberty Township, OH (US); Ronald David Turner, Walton, KY (US); Chung Wai Smiley Chiu, Hong Kong (CN)

(73) Assignee: The Procter & Gamble Company, Cincinnati, OH (US)

( * ) Notice: Subject to any disclaimer, the term of this patent is extended or adjusted under 35 U.S.C. 154(b) by 678 days.

(21) Appl. No.: 16/180,060

(22) Filed: Nov. 5, 2018

(65) Prior Publication Data
US 2019/0070329 A1    Mar. 7, 2019

Related U.S. Application Data

(63) Continuation of application No. PCT/CN2016/104322, filed on Nov. 2, 2016.

(51) Int. Cl.
*A61L 9/03* (2006.01)
*A01M 1/20* (2006.01)
(Continued)

(52) U.S. Cl.
CPC ......... *A61L 9/032* (2013.01); *A01M 1/2072* (2013.01); *A01M 1/2077* (2013.01); *A61L 9/037* (2013.01);
(Continued)

(58) Field of Classification Search
CPC ...... B01F 3/04085; A61L 9/127; A61L 9/122; A61L 9/032; A61L 9/037;
(Continued)

(56) References Cited

U.S. PATENT DOCUMENTS 3,131,733 A * 5/1964 Monahon ............... B65D 83/42
                                                        141/354
3,181,737 A * 5/1965 Chaucer ............... B65D 83/687
                                                        141/20
(Continued)

FOREIGN PATENT DOCUMENTS

EP          2409716 A2    1/2012
GB          2492635 A     1/2013
(Continued)

OTHER PUBLICATIONS

International Search Report and Written Opinion; Application No. CN2016/104322; dated Aug. 3, 2017; 7 pages.
(Continued)

*Primary Examiner* — Eric S Stapleton
(74) *Attorney, Agent, or Firm* — Carolyn S. Powell; George H. Leal; Abbey A. Lopez

(57) ABSTRACT

A volatile composition dispenser and a method of dispensing a volatile composition is provided. The volatile composition dispenser includes a reservoir for containing a volatile composition and a transport member having a first end portion and an opposing second end portion, and an evaporative surface. The first end portion of the transport member is in fluid communication with the reservoir and the second end portion of the transport member is in fluid communication with the evaporative surface. The volatile composition dispenser also includes an air pump in gaseous communication with the reservoir.

13 Claims, 7 Drawing Sheets

(51) Int. Cl.
*A61L 9/12* (2006.01)
*B01F 23/21* (2022.01)
*B05B 7/00* (2006.01)
*B05B 7/16* (2006.01)
*B05B 7/24* (2006.01)

(52) U.S. Cl.
CPC ............... *A61L 9/122* (2013.01); *A61L 9/127* (2013.01); *B01F 23/215* (2022.01); *B05B 7/0081* (2013.01); *B05B 7/162* (2013.01); *B05B 7/2494* (2013.01); *A61L 2209/111* (2013.01); *A61L 2209/133* (2013.01)

(58) Field of Classification Search
CPC ......... A61L 2209/111; A61L 2209/133; B05B 7/2494; B05B 7/0081; B05B 7/162; A01M 1/2072; A01M 1/2077
USPC .......................................................... 392/395
See application file for complete search history.

(56) References Cited

U.S. PATENT DOCUMENTS

| | | | | |
|---|---|---|---|---|
| 3,337,091 A * | 8/1967 | Bartels | ................... | B65D 83/42 222/95 |
| 3,357,603 A * | 12/1967 | Kitabayashi | ........... | B65D 83/42 222/402.16 |
| 3,363,810 A * | 1/1968 | Meshberg | ............... | B65D 83/42 222/484 |
| 3,365,105 A * | 1/1968 | Krizka | ................... | B65D 83/42 222/394 |
| 3,366,148 A * | 1/1968 | Mizuguchi | ............ | B65B 31/003 141/3 |
| 3,482,929 A * | 12/1969 | Gentil | .................. | B01D 1/0082 239/45 |
| 3,559,701 A * | 2/1971 | Wittersheim | .......... | B65D 83/42 141/303 |
| 3,613,960 A * | 10/1971 | Beard | .................... | B65D 83/42 222/402.1 |
| 3,718,165 A * | 2/1973 | Grothoff | ................ | B65D 83/42 141/20 |
| 3,817,297 A * | 6/1974 | King | ....................... | B65D 83/42 141/20 |
| 3,863,846 A * | 2/1975 | Keller, Jr. | ........... | B02C 19/0056 241/1 |
| 3,874,563 A * | 4/1975 | Schwartzman | ........ | B65D 47/42 222/496 |
| 4,093,123 A * | 6/1978 | Maran | .................... | B65D 83/64 141/20 |
| 4,174,811 A * | 11/1979 | Binder | ................... | B65D 83/66 222/402.18 |
| 4,200,229 A * | 4/1980 | Spector | ............... | B05B 11/1001 239/289 |
| 4,200,607 A * | 4/1980 | Suzuki | ................. | G01N 35/025 422/81 |
| 4,257,427 A * | 3/1981 | Bucalo | ................ | A61B 10/0045 435/309.1 |
| 4,346,059 A * | 8/1982 | Spector | .................... | A61L 9/03 239/57 |
| 4,473,097 A * | 9/1984 | Knickerbocker | .. | B65D 81/3211 222/215 |
| 4,512,933 A * | 4/1985 | Harden | ................... | A61L 9/122 239/326 |
| 4,570,532 A * | 2/1986 | Labelle | ..................... | F24F 7/06 236/49.1 |
| 4,582,807 A * | 4/1986 | Veeraraghavan | ........ | C12Q 1/18 435/39 |
| 4,623,337 A * | 11/1986 | Maurice | ............. | B05B 11/1015 604/298 |
| 4,852,807 A * | 8/1989 | Stoody | ................... | B65D 83/46 239/576 |
| 4,921,071 A * | 5/1990 | Lonnborg | ............. | F01M 11/06 184/45.1 |
| 5,179,982 A * | 1/1993 | Berube | .................. | B65D 83/42 222/105 |
| 5,281,401 A * | 1/1994 | Bryson, Sr. | ............... | F24F 3/12 222/638 |
| 5,343,904 A * | 9/1994 | Kaeser | .................. | B65B 31/003 141/346 |
| 5,388,620 A * | 2/1995 | Lasserre | ................ | C04B 18/10 141/3 |
| 5,449,117 A * | 9/1995 | Muderlak | ............... | E03D 9/005 239/521 |
| 5,524,468 A * | 6/1996 | Jentzsch | ................ | B21D 51/26 72/379.4 |
| 5,524,680 A * | 6/1996 | de Laforcade | ...... | B05B 11/0056 141/22 |
| 5,595,324 A * | 1/1997 | Brown | .................. | A47K 5/1202 261/DIG. 65 |
| 5,791,527 A * | 8/1998 | Giuffredi | ............ | B05B 11/0056 222/525 |
| 5,819,986 A * | 10/1998 | Last | .................... | B05B 11/1004 222/105 |
| 5,832,965 A * | 11/1998 | Fasse | ........................ | B65B 3/12 141/20 |
| 5,840,246 A * | 11/1998 | Hammons | ................. | A61L 9/03 239/54 |
| 5,879,095 A * | 3/1999 | Gueret | .................. | A45D 40/262 401/172 |
| 5,949,522 A * | 9/1999 | Manne | .................... | A61L 9/122 261/DIG. 65 |
| 6,050,025 A * | 4/2000 | Wilbanks | .............. | A01M 1/223 43/112 |
| 6,170,717 B1 * | 1/2001 | Di Giovanni | .......... | B65D 83/54 222/402.2 |
| 6,308,867 B1 * | 10/2001 | Wolter | ............... | B05B 11/1026 222/321.6 |
| 6,390,453 B1 * | 5/2002 | Frederickson | .... | B01F 35/71791 261/78.2 |
| 6,418,978 B2 * | 7/2002 | Bailly | .................. | B05B 11/0097 141/2 |
| 6,435,231 B1 * | 8/2002 | Cooper | ................ | B65D 83/682 141/369 |
| 6,533,482 B1 * | 3/2003 | Byun | .................... | A45D 34/04 401/265 |
| 6,569,387 B1 * | 5/2003 | Furner | .................. | A01M 1/2038 239/289 |
| 6,607,012 B2 * | 8/2003 | Yquel | ..................... | B65D 83/34 141/3 |
| 6,622,662 B1 * | 9/2003 | Wolpert | ................... | A61L 9/03 122/366 |
| 6,681,961 B2 * | 1/2004 | Pares Montaner | ........................ B05B 11/1061 222/321.9 |
| 6,857,806 B2 * | 2/2005 | Harrison | ............... | A45D 34/041 401/219 |
| 6,863,093 B2 * | 3/2005 | Garcia | ................ | B05B 11/0097 141/2 |
| 6,967,008 B1 * | 11/2005 | Barnes | .................. | A01M 29/12 422/186.07 |
| 7,066,674 B2 * | 6/2006 | Gueret | .................. | B05B 11/026 401/125 |
| 7,135,169 B2 * | 11/2006 | Maleeny | ................. | A61L 9/14 424/47 |
| 7,249,719 B2 * | 7/2007 | He | ......................... | A61L 9/035 239/45 |
| 7,377,296 B2 * | 5/2008 | Gueret | ................ | A45D 34/042 401/125 |
| 7,377,493 B2 * | 5/2008 | Thomas | .................... | A61L 9/12 261/DIG. 89 |
| 7,490,815 B2 * | 2/2009 | Tollens | ................ | B05B 17/0646 261/81 |
| 7,757,431 B2 * | 7/2010 | Welch | .................... | A01M 1/04 43/112 |
| 7,870,977 B2 * | 1/2011 | Pietrowski | .......... | B05B 11/0078 222/321.2 |
| 8,016,270 B2 * | 9/2011 | Chen | ........................ | F24F 7/007 261/78.2 |

(56) References Cited

U.S. PATENT DOCUMENTS

| | | | | |
|---|---|---|---|---|
| 8,079,388 B2* | 12/2011 | Turgeman | | B05B 11/0038 141/351 |
| 8,382,008 B1* | 2/2013 | Ricciardi | | G05B 15/02 239/338 |
| 9,259,750 B2* | 2/2016 | Johnson | | A01M 1/205 |
| 9,266,072 B2* | 2/2016 | Ingledew | | A61L 9/127 |
| 9,339,578 B2* | 5/2016 | Ingledew | | A01M 1/2033 |
| 9,486,822 B2* | 11/2016 | Johnson | | A01M 1/205 |
| 9,603,357 B2* | 3/2017 | Marchetti | | A61L 9/122 |
| 9,718,072 B2* | 8/2017 | Bruder | | B05B 11/00442 |
| 2002/0168301 A1* | 11/2002 | Channer | | A61L 9/127 422/120 |
| 2003/0005620 A1* | 1/2003 | Ananth | | A61L 9/02 43/125 |
| 2003/0206834 A1* | 11/2003 | Chiao | | A61L 9/145 428/905 |
| 2004/0028785 A1* | 2/2004 | Langourieux | | A23L 27/80 426/386 |
| 2004/0076462 A1* | 4/2004 | Grandmottet | | B05B 11/0056 401/55 |
| 2005/0036823 A1* | 2/2005 | Butcher | | A45D 40/262 401/265 |
| 2005/0127207 A1* | 6/2005 | Kubby | | A01M 1/2077 239/303 |
| 2005/0129568 A1* | 6/2005 | Kubby | | A61L 9/14 422/5 |
| 2005/0130747 A1* | 6/2005 | Kubby | | A61L 9/14 463/48 |
| 2005/0155985 A1* | 7/2005 | Meyer | | A61L 9/037 222/146.2 |
| 2005/0185940 A1* | 8/2005 | Joshi | | A61L 9/12 392/390 |
| 2005/0199742 A1* | 9/2005 | Maat | | A01N 25/34 239/34 |
| 2006/0022064 A1* | 2/2006 | Triplett | | A01M 1/2044 239/44 |
| 2006/0045359 A1* | 3/2006 | Chen | | H04N 19/184 375/E7.184 |
| 2006/0075729 A1* | 4/2006 | He | | A61L 9/16 55/385.1 |
| 2006/0110144 A1* | 5/2006 | Fellows | | A61L 9/037 392/395 |
| 2006/0118574 A1* | 6/2006 | Anderson | | B67C 3/30 222/1 |
| 2006/0175425 A1* | 8/2006 | McGee | | A61L 9/127 239/44 |
| 2006/0261179 A1* | 11/2006 | Davies | | A61L 9/22 239/45 |
| 2006/0269455 A1* | 11/2006 | Planker | | A61L 9/04 422/123 |
| 2006/0292304 A1* | 12/2006 | Tisone | | B01L 3/0265 427/256 |
| 2007/0138326 A1* | 6/2007 | Hu | | A01M 1/2038 239/690 |
| 2007/0204387 A1* | 9/2007 | Cornelius | | A01M 1/2044 4/223 |
| 2007/0210183 A1* | 9/2007 | Kubby | | A01M 1/2077 239/102.1 |
| 2007/0217771 A1* | 9/2007 | Granger | | A01M 1/2033 392/386 |
| 2008/0019862 A1* | 1/2008 | White | | A61L 9/03 422/123 |
| 2008/0087737 A1* | 4/2008 | Dunne | | A61L 9/12 239/1 |
| 2008/0149665 A1* | 6/2008 | Hafer | | A01M 1/2077 239/128 |
| 2008/0251598 A1* | 10/2008 | Ross | | A01M 1/2077 239/44 |
| 2009/0184175 A1* | 7/2009 | Blankenstein | | A61L 9/04 239/49 |
| 2009/0220222 A1* | 9/2009 | Rabin | | A61M 16/109 392/394 |
| 2010/0086448 A1* | 4/2010 | Faber | | A47G 7/06 422/120 |
| 2010/0187327 A1* | 7/2010 | Irvin | | B60H 3/0007 239/47 |
| 2010/0243754 A1* | 9/2010 | Harris | | A61L 9/14 239/34 |
| 2010/0270391 A1* | 10/2010 | Allison | | C11C 5/00 239/44 |
| 2011/0072711 A1* | 3/2011 | Black | | A61L 9/122 43/107 |
| 2011/0091354 A1* | 4/2011 | Schwartz | | F24F 8/24 422/111 |
| 2011/0114744 A1* | 5/2011 | Ricciardi | | A61L 2/22 239/4 |
| 2011/0133001 A1* | 6/2011 | Cooper | | B05B 7/066 239/418 |
| 2011/0133004 A1* | 6/2011 | Thomason | | B05B 7/1209 239/690 |
| 2011/0137268 A1* | 6/2011 | Thomason | | B05B 7/066 604/291 |
| 2011/0163178 A1* | 7/2011 | Planker | | A61L 9/013 165/104.34 |
| 2011/0309113 A1* | 12/2011 | Hui | | B65D 83/42 222/402.16 |
| 2012/0018530 A1* | 1/2012 | Blaylock | | A61L 9/14 239/338 |
| 2012/0168971 A1* | 7/2012 | Hansen | | A47L 11/4086 261/78.2 |
| 2012/0201522 A1* | 8/2012 | Stauffer | | A63J 5/025 392/386 |
| 2012/0211515 A1* | 8/2012 | An | | A61L 9/14 222/61 |
| 2012/0211523 A1* | 8/2012 | An | | A61L 9/127 222/173 |
| 2012/0230864 A1* | 9/2012 | An | | A01M 1/2077 422/3 |
| 2014/0079597 A1* | 3/2014 | Segura Rius | | A61L 9/015 422/123 |
| 2014/0138458 A1* | 5/2014 | Stephenson | | A01M 1/2077 239/44 |
| 2014/0294667 A1* | 10/2014 | Sevy | | A61L 9/00 422/4 |
| 2014/0301722 A1* | 10/2014 | Stephenson | | A61L 9/122 392/395 |
| 2014/0363333 A1* | 12/2014 | Carr | | A61L 9/16 422/123 |
| 2015/0019029 A1* | 1/2015 | Chandler | | G06Q 10/06314 700/283 |
| 2015/0130088 A1* | 5/2015 | Joshi | | A61L 9/122 239/34 |
| 2015/0297776 A1* | 10/2015 | Conroy | | G08B 13/22 239/11 |
| 2015/0352577 A1* | 12/2015 | Burrowes | | B05B 11/1056 239/304 |
| 2016/0067367 A1* | 3/2016 | Jin | | A61L 9/042 239/152 |
| 2016/0286782 A1* | 10/2016 | Manhas | | A01M 1/2044 |
| 2016/0310624 A1* | 10/2016 | Wynalda, Jr. | | A01M 1/2088 |
| 2017/0023922 A1* | 1/2017 | Chandler | | G05B 19/0426 |
| 2017/0056915 A1* | 3/2017 | Hayden | | F24F 3/14 |
| 2017/0122616 A1* | 5/2017 | Calabro | | F24F 11/30 |
| 2018/0117203 A1* | 5/2018 | Gruenbacher | | A01M 1/2077 |

FOREIGN PATENT DOCUMENTS

| | | |
|---|---|---|
| JP | H0529984 U | 4/1993 |
| JP | H0618061 A | 1/1994 |
| JP | 3000741 U | 8/1994 |
| JP | 2001062890 A | 3/2001 |
| JP | 2004159875 A | 6/2004 |
| JP | 2004236948 A | 8/2004 |
| JP | 2006524064 A | 10/2006 |
| JP | 2009502442 A | 1/2009 |
| JP | 2011115053 A | 6/2011 |
| JP | 2011184486 A | 9/2011 |

(56) References Cited

FOREIGN PATENT DOCUMENTS

| | | |
|---|---|---|
| KR | 970011444 B1 | 7/1997 |
| WO | 9112992 A1 | 9/1991 |
| WO | 2015158970 A1 | 10/2015 |

OTHER PUBLICATIONS

All Office Actions, U.S. Appl. No. 15/368,981.
P&G Case Search Report; PCT/CN2016/10433; dated Feb. 11, 19; 8 Pages.

* cited by examiner

VOLATILE COMPOSITION DISPENSER HAVING AN AIR PUMP AND A METHOD OF DELIVERING A VOLATILE COMPOSITION TO AN EVAPORATIVE SURFACE USING THE SAME

FIELD

The present disclosure is directed to a volatile composition dispenser, and, more particularly, is directed to a volatile composition dispenser that utilizes an air pump and a method of delivering a volatile composition to an evaporative surface using the same.

BACKGROUND

There are a variety of volatile composition dispensers available on the market today, including aerosol and pump sprayers, non-energized and energized dispensers that utilize a wick, diffusers, and the like, for delivering a volatile composition, such as a perfume composition, into the air. Energized dispensers that use a wick to deliver a volatile composition into the air may include a heater or fan to assist in the evaporation of the volatile composition and may be powered through a wall outlet or may be battery-powered. Such wick-based dispensers provide a relatively simple construction, are easy for consumers to operate, and provide cost effective means of delivery a volatile composition into the air. However, wick-based volatile composition dispensers may have drawbacks. For example, perfume compositions may include a mixture of perfume raw materials having a range of volatilities. Heavier or less volatile perfume raw materials can stick to the wick and ultimately cause the wick to become blocked with perfume raw materials. As a result, the character of the perfume composition that is volatilized from the wick-based dispenser can change over time and also the flow rate may decline over time as the wick becomes blocked.

Thus, it would be beneficial to provide a volatile composition dispenser that maintains a more consistent flow rate over time. Moreover, it would be beneficial over time to provide a volatile composition dispenser that delivers a more uniform perfume character profile over time.

SUMMARY

"Combinations:"
A. A volatile composition dispenser comprising:
   a reservoir for containing a volatile composition, the reservoir having an air inlet and a liquid outlet that is spaced apart from the air inlet,
   a transport member having a first end portion and an opposing second end portion, wherein the first end portion is in liquid communication with the reservoir and the second end portion extends through the liquid outlet,
   an evaporative surface disposed proximal to the second end portion of the transport member; and
   an air pump in gaseous communication with the air inlet of the reservoir.
B. The dispenser of Paragraph A further comprising a heater in communication with the evaporative surface.
C. The dispenser of any of Paragraphs A through B further comprising a fan disposed adjacent to the evaporative surface.
D. The dispenser of any of Paragraphs A through C further comprising a cartridge and a housing, the cartridge comprising the reservoir and transport member, and wherein the cartridge is releasably connectable with the housing.
E. The dispenser of Paragraph D, wherein the evaporative surface is connected with the cartridge.
F. The dispenser of Paragraph D or Paragraph E, wherein the evaporative surface comprises a material selected from the group consisting of metal, plastic, glass, and combinations thereof.
G. The dispenser of any of Paragraphs A through F, wherein the evaporative surface is air permeable.
H. The dispenser of any of Paragraphs A through H further comprising a controller in electrical communication with the air pump and a power source that is in electrical communication with the air pump and controller.
I. The dispenser of Paragraph H wherein the transport member further comprises a restriction member disposed in the second end portion.
J. A method of dispensing a volatile composition, the method comprising the steps of:
   pumping air into an interior of a cartridge to pressurize the cartridge, the cartridge containing a volatile composition;
   directing the volatile composition to an evaporative surface; and
   evaporating the volatile composition from the evaporative surface.
K. The method of Paragraph J further comprising the step of: heating the air adjacent to the evaporative surface.
L. The method of Paragraph J or Paragraph K further comprising the step of directing a volume of air over or around the evaporative surface to direct the evaporating volatile composition into the air.
M. The method of any of Paragraphs J through L, wherein the step of pumping air into a cartridge comprises intermittently pumping air into the cartridge to pressurize the cartridge, and wherein the step of directing the volatile composition to an evaporative surface comprises intermittently directing the volatile composition to the evaporative surface.
N. The method of any of Paragraphs J through N, wherein the step of pumping air into a cartridge comprises pumping air into the cartridge to pressurize the cartridge with an air pump, wherein the air pump does not contact the volatile composition.
O. The method of any of Paragraphs J through N, wherein the air pump pressurizes the cartridge by at least about 0.5 kPa.

DETAILED DESCRIPTION

Figure 1:
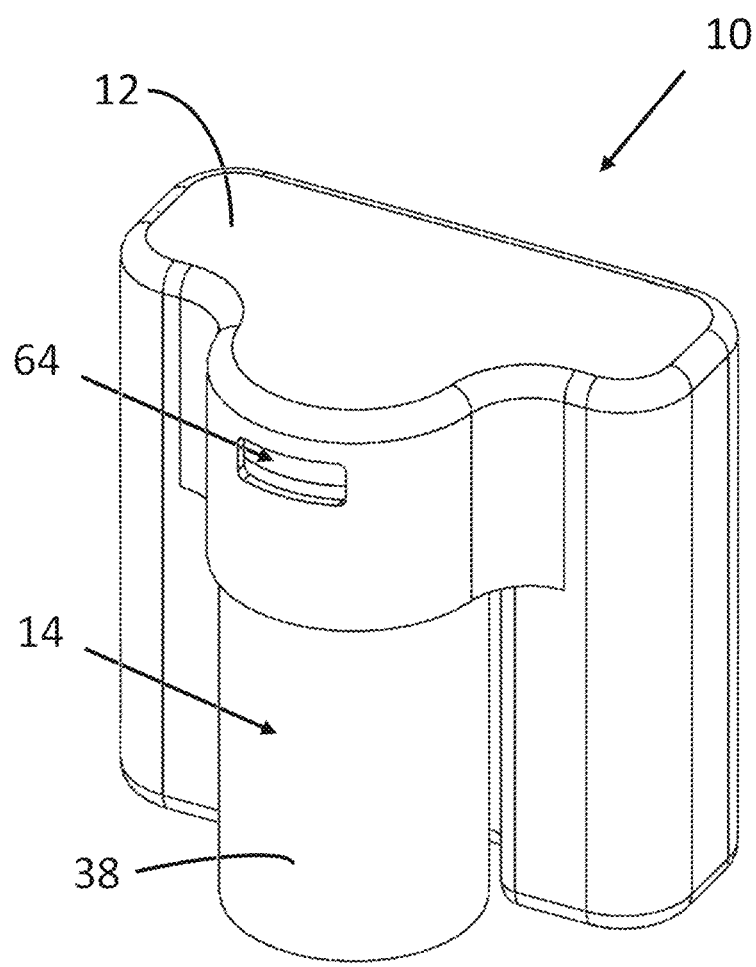
FIG. 1 is a front, perspective view of an exemplary volatile composition dispenser.

The present disclosure provides a volatile composition dispenser having a reservoir, a transport member, an air pump, and an evaporation element having an evaporative surface. The air pump is configured to continuously or intermittently deliver doses of the volatile composition from the reservoir to the evaporative surface through the transport member.

The air pump is configured to only contact the air and not the volatile composition. As a result, the air pump is less likely to corrode and, therefore, may have a relatively long-life span.

Moreover, since the air pump delivers doses of the volatile composition to the evaporative surface over time, the intensity and character of the evaporated volatile composition may remain substantially uniform over time. The evaporation flow rate may be maintained at a substantially constant rate over time.

The volatile composition dispenser may include a heater to assist in the evaporation of the volatile composition from the evaporative surface.

The volatile composition may include a fan to assist in the dispersion of the evaporated volatile composition throughout a room.

The volatile composition may comprise various materials. For example, the volatile composition may include one or more perfume raw materials, diluents, solvents, aqueous carriers, and the like. The volatile composition may include at least 30 wt. %, alternatively at least 40 wt. %, alternatively at least 50 wt. %, alternatively at least 60 wt. %, alternatively at least 75 wt. % of perfume raw materials, by total weight of the volatile composition. The volatile composition may include, in addition to perfume or as an alternative to perfume, malodor counteractants, insect repellants, and the like.

With reference to FIGS. 1-4, a volatile composition dispenser 10 may include a housing 12, a cartridge 14, a transport member 16 in fluid communication with the cartridge 14, and an evaporation member 18 having an outer surface 20 herein referred to as an "evaporative surface" 20 that is in fluid communication with the transport member 16. The volatile composition dispenser 10 includes an air pump 22 in gaseous communication with the cartridge 14. The volatile composition dispenser 10 of FIG. 1 has a power source 28 in the form of an electrical outlet plug. As will be discussed in more detail below, the air pump pressurizes the cartridge, causing the volatile composition contained therein to flow through the transport member to the evaporative surface where the volatile composition evaporates into the air.

The volatile composition dispenser 10 may also include a heater 24 and a fan 26 such as shown in FIGS. 1-4.

The housing 12 may be configured to contain many or all of the elements of the volatile composition dispenser 10. The housing 12 may be comprised of a single element or from multiple elements that are joined together to define an interior chamber 30. The housing 12 may take any shape and may be composed of various materials, such as plastic, metal, resin, and the like.

Figure 2:
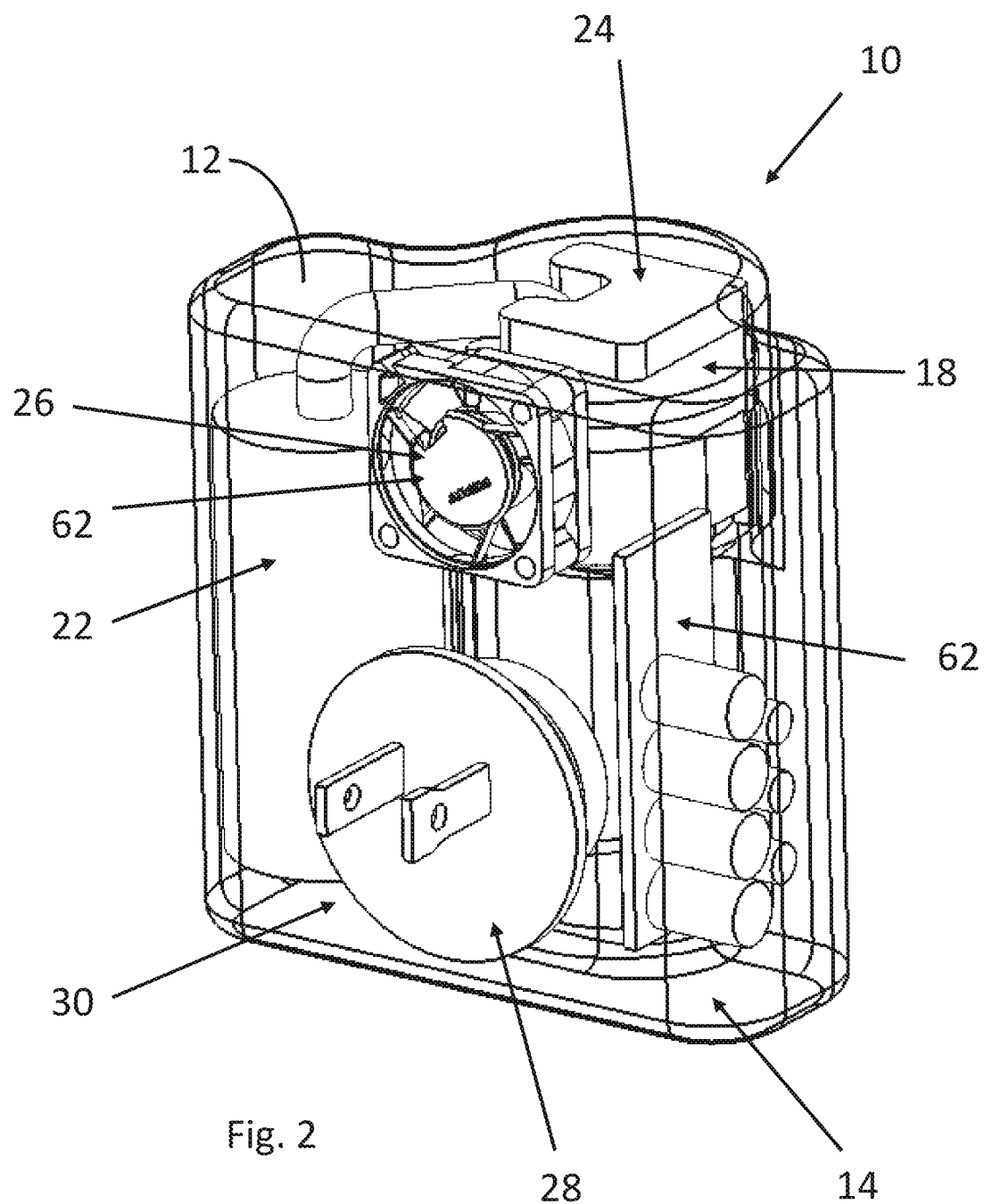
FIG. 2 is a back, perspective view of an exemplary volatile composition dispenser, where the housing of the volatile composition dispenser is shown as translucent in order to view the internal components of the volatile composition dispenser.
Figure 3:
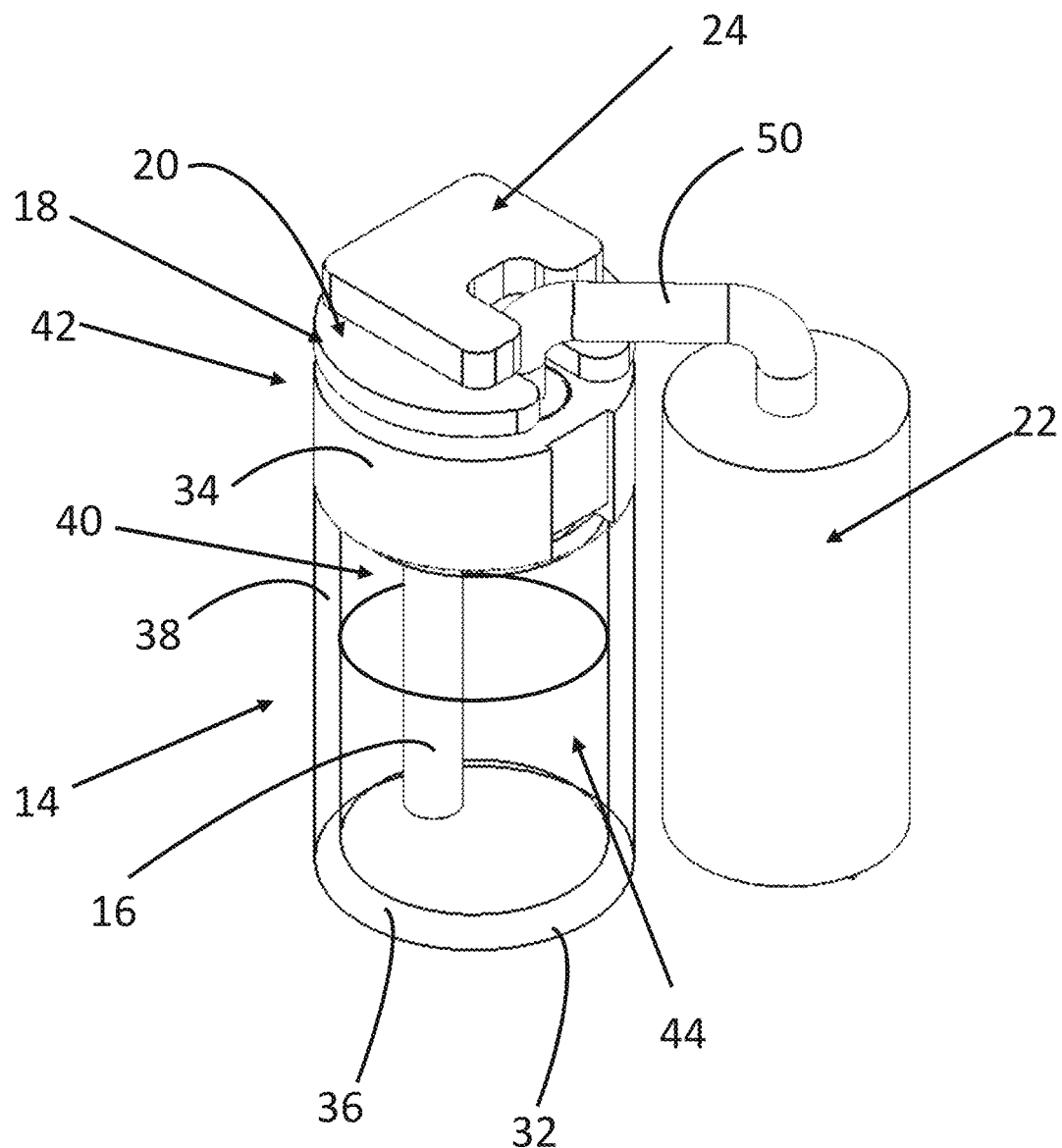
FIG. 3 is a perspective view of a cartridge, air pump, evaporation member, and heater of an exemplary volatile composition dispenser.
Figure 4:
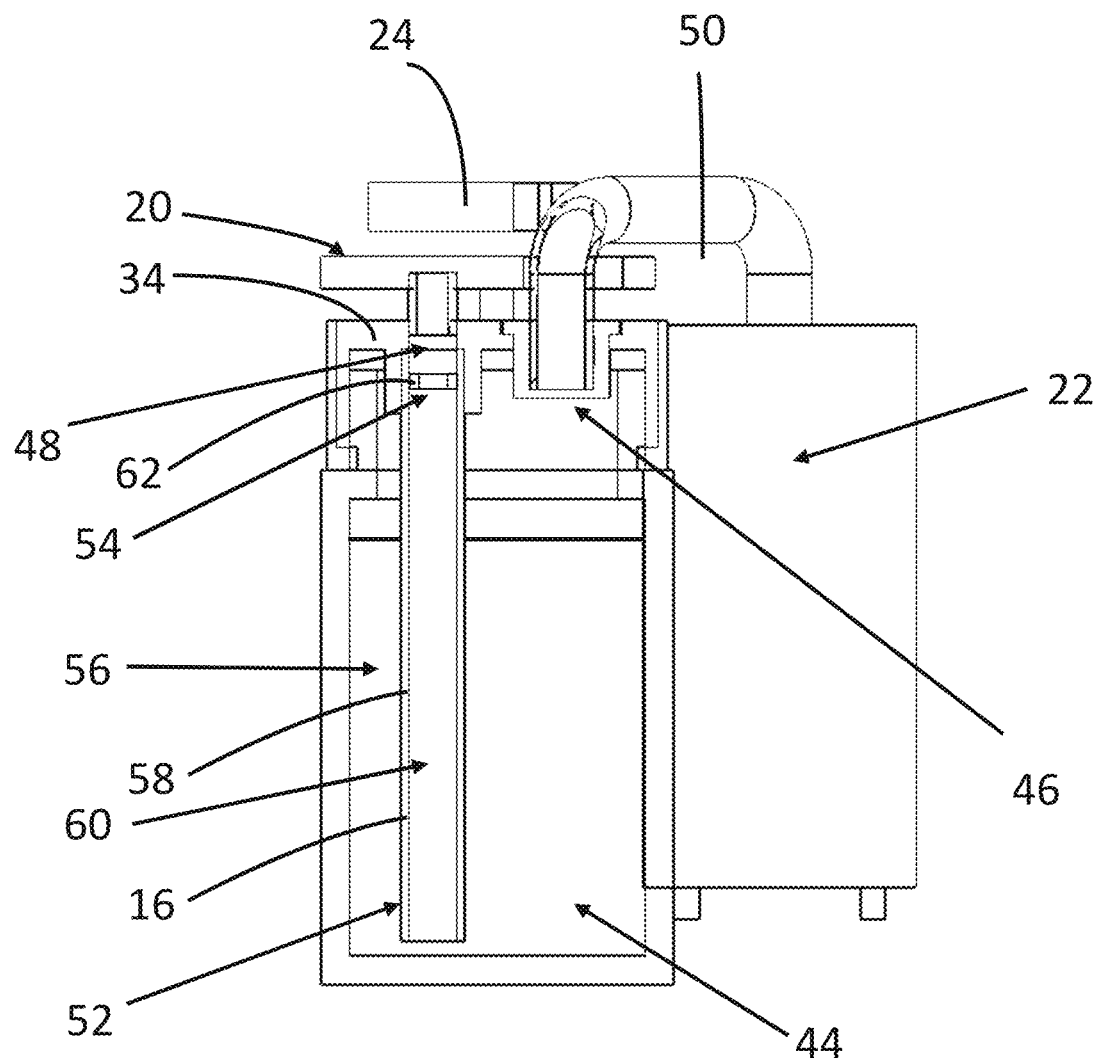
FIG. 4 is a side, elevation view of a cartridge, air pump, evaporation member, and heater of an exemplary volatile composition dispenser.

With reference to FIGS. 2-4, the cartridge 14 is configured to contain a volatile composition 44. The cartridge 14 may include a reservoir 32 and a cap 34 for enclosing the reservoir 32. The reservoir 32 may include a base 36 and at least one sidewall 38. The cartridge 14 defines an interior 40 and an exterior 42. The interior 40 of the cartridge 14 is sealed from the exterior 42 of the cartridge 14 to prevent leaking of the volatile composition 44 out of the cartridge 14 and to allow the generation of air pressure inside the cartridge 14 to cause the volatile composition 44 to dispense onto the evaporative surface 20. The cartridge 14 includes an air inlet 46 that is in gaseous communication with the air pump 22. The cartridge 14 also includes a volatile composition outlet 48 where the volatile composition 44 is directed from the cartridge 14 to the evaporative surface 20 though the transport member 16. The air inlet 46 and/or the composition outlet 48 may, but is not required to, be disposed in the cap 34 of the cartridge 14 such as shown FIGS. 2 and 3.

The cartridge 14 may be releasably connectable with the housing 12 or may be permanently connected with the housing 12. The housing 12 may be configured to replace the cartridges 14 once a cartridge 14 is empty. The cartridge 14 may connect with the housing 12 in various ways. For example, the cap 34 of the cartridge 14 may be releasably connectable with the housing 12. The cartridge 14 may be slideably or rotatably connectable or spring loaded with the housing 12.

The cartridge 14 may be composed of various materials, including plastic, glass, metal, a composite material, the like, and combinations thereof. The reservoir 32 and cap 34 of the cartridge 14 may be configured as one element or may be configured as separate elements that are joined and sealed together. The cap 34 and the reservoir 32 may be composed of the same materials or may be composed of different materials. The cap 34 and/or reservoir 32 may be transparent, translucent, or opaque. While the cartridge 14 shown in FIGS. 2 and 3 is substantially cylindrical, it is to be appreciated that the cartridge 14may take various different common shapes such as cube or egg-shaped, or any unique shapes. The reservoir 32 and the cap 34 may be integrally formed or may be separate components that are joined together.

With reference to FIGS. 3 and 4, a transfer member 16 is in fluid communication with the cartridge 14 for delivering the volatile composition 44 contained within the cartridge 14 to the evaporative surface 20. The transport member 16 may be in fluid communication with the base 36 of the reservoir 32 in order to dispense substantially all of the volatile composition contained within the reservoir 32. The transport member 16 may be defined by a first end portion 52, a second end portion 54, and a central portion 56 separating the first and second end portions 52 and 54. The first end portion 52 of the transport member 16 may be disposed in the cartridge 14 and may be in fluid communication with the volatile composition 44. At least a portion of the transport member 16 is disposed within the interior 40 of the cartridge 14. A portion of the transport member 16 may extend to the exterior 42 to the cartridge 14. The first end portion 52 may contact the base 36 of the reservoir 32. The transport member 16 may be configured to direct the volatile composition 44 from the reservoir 32 to the evaporative surface 20.

The transport member 16 may be configured in various ways. For example, the transport member may be configured as a tube having an outer wall 58 and a hollow interior 60 such as shown in FIGS. 3 and 4. The tube may be in the form of a capillary tube. The transport member 16 may be composed of various materials, including plastic, glass, metal, rubber, silicone, and combinations thereof. The transport member may also be comprised of a porous or semi-porous wick that is wrapped in a non-air permeable outer wrap. The wick may be composed of various materials and methods of construction, including, but not limited to, bundled fibers which are compressed and/or formed into various shapes via overwrap (such as a non-woven sheet over-wrap) or made of sintered plastics such as PE, HDPE or other polyolefins. For example, the wick may be made from a plastic material such as polyethylene or a polyethylene blend.

With reference to FIGS. 3 and 4, the transport member may be configured to have a fluid restricting member 62 disposed at the second end portion. The fluid restricting member may comprise, for example, a simple orifice or a porous member. The evaporation member, if comprising a porous material, may serve also as the fluid restricting member. The transport member may be a tube having an inner diameter of, for example, 2 mm. The fluid restricting member may be an orifice having a diameter of, for example, 0.5 mm.

As discussed above, and with reference to FIGS. 3-4, the volatile composition dispenser 10 may also include an evaporation member 18 having an evaporative surface 20. The volatile composition evaporates from the evaporative surface 20 into the air. The evaporative surface 20 may be disposed proximate to the second end portion 54 of the transport member 16. The transport member 16 may deliver the volatile composition 44 from the reservoir 32 to the evaporative surface 20. The evaporative surface 20 may take various different forms.

For example, the evaporation member 18, such as the evaporation member 18 of FIGS. 3-4 shown for illustrative purposes only, may be configured as a porous, semi-porous, and/or air permeable substrate such as a sponge or wick. Where the evaporative member 18 comprises a porous, semi-porous or air-permeable substrate, the volatile composition 44 may absorb into the evaporation member 18 before volatilizing into the air from the evaporative surface 20.

Figure 5:
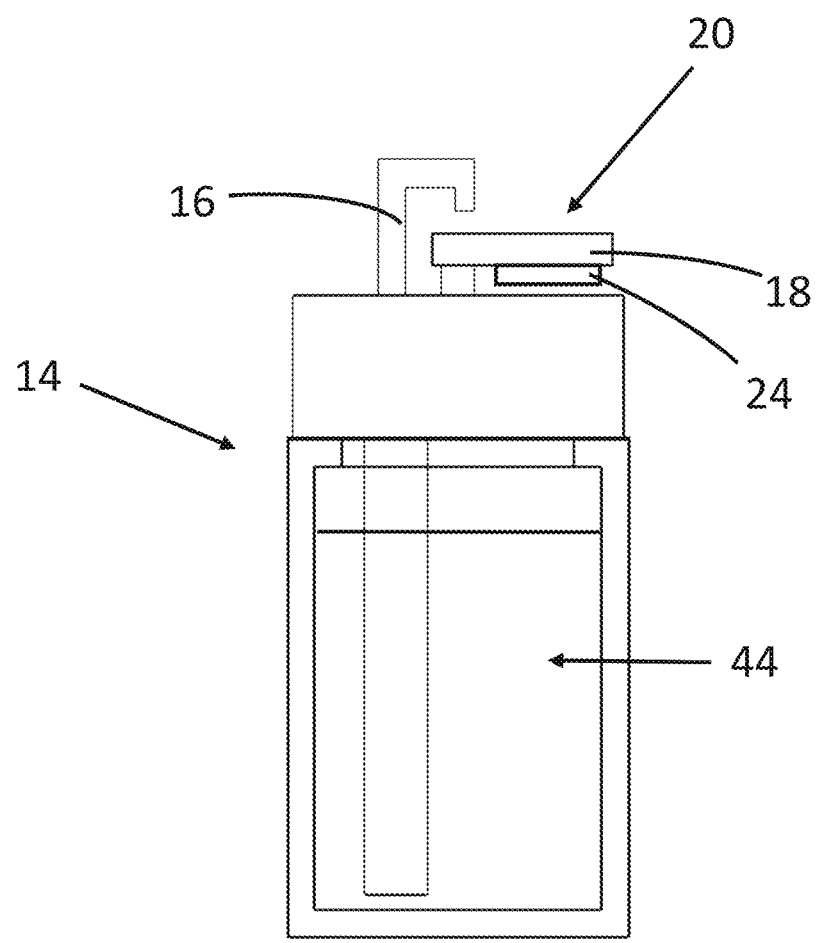
FIG. 5 is a side, elevation view of a cartridge, air pump, evaporation member, and heater of an exemplary volatile composition dispenser.

With reference to FIG. 5, the evaporation member 18 may be a substantially non-porous or non-air permeable substrate, such as a plate, bowl, dish, that is comprised of materials such as metal, glass, plastic, and combinations thereof. As shown in FIG. 5, the volatile composition may flow down onto the evaporative surface 20. Where the evaporative member 18 comprises a substantially non-porous or non-air permeable substrate, the volatile composition 44 may be dispensed onto the evaporative surface 20 and may be disposed on the evaporative surface 20 without absorbing into the evaporation element 18 until the volatile composition 44 volatizes into the air. For ease of view, the volatile composition dispenser of FIG. 5 is shown without an air pump.

Figure 6:
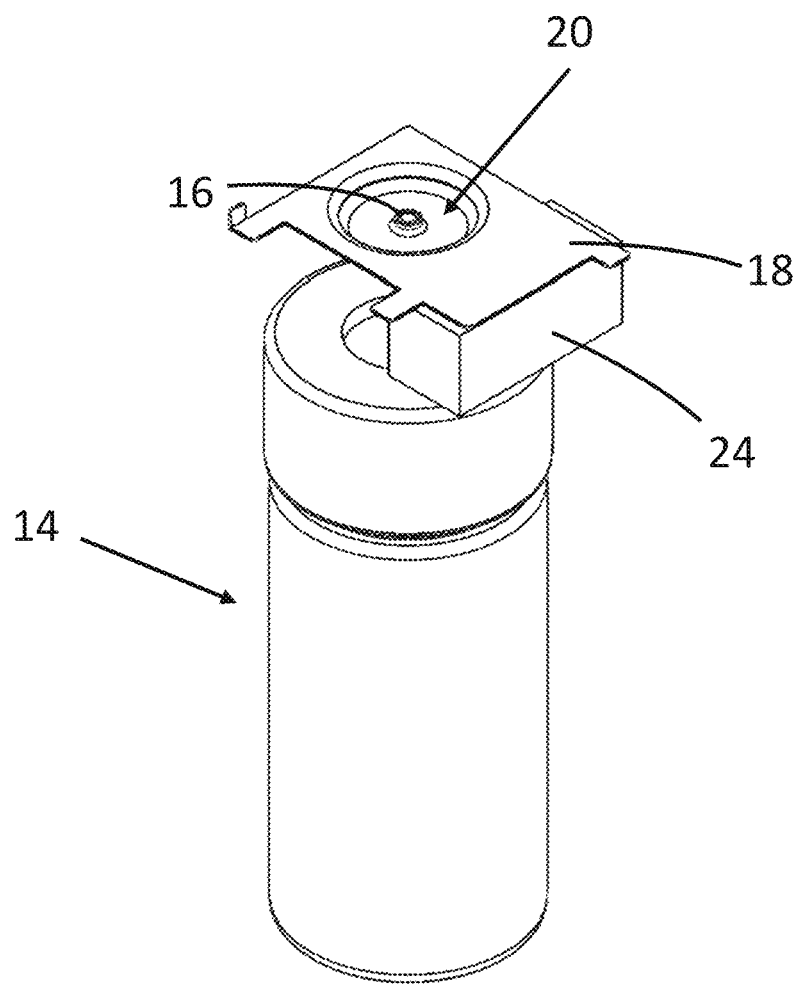
FIG. 6 is a perspective view of a cartridge, air pump, evaporation member, and heater of an exemplary volatile composition dispenser.

With reference to FIG. 6, the transport member 16 and the evaporative surface 20 may be configured such that the volatile composition flows from the transport member 16 onto the surrounding evaporative surface 20 that is shaped as a bowl or plate.

FIGS. 2 and 3 illustrate that the evaporation member 18 may be connected, either fixedly or releasably, with the cartridge 14. However, it is to be appreciated that the evaporation member 18 may be disposed adjacent to the cartridge 14 without being connected with the cartridge 14.

With reference back to FIG. 2, the volatile composition dispenser 10 includes an air pump 22. The air pump 22 is in gaseous communication with the reservoir 32 through the air inlet 46. The air pump is 22 configured to pump air into the interior 40 of the cartridge 14 to pressurize the interior 40 of the cartridge 14, which causes the volatile composition 44 to flow through the transport member 16 and onto the evaporative surface 20. The air pump 22 can take many different forms such as, but are not limited to, piezo, diaphragm, squirrel, radial, piston pumps. The air pump may also be in the form of a pressurized gas cartridge, such as carbon dioxide, or in the form of a fuel cell. The air pump 22 may include a connector 50 that connects the air pump 22 with the cartridge 14. The air pump 22 only pumps air and does not come into contact with the volatile composition 44, thereby limiting corrosion and wear on the air pump 22. Exemplary air pumps may include, for example, DC air pump, or a DC mini air pump.

The air pump may deliver pressure to the reservoir that is equal to the liquid column created by the fluid transport member, which may be on the order of at least about 0.5 kilopascals (kPa). A more preferred embodiment would have an air pump that delivers a multiple of this minimum pressure, for example ten times the reservoir's liquid column, or 5 kPa. A higher pressure will minimize the transit time through the transport member, and thus result in more consistent doses to the evaporating surface. The pressure should not be so high as to make regulation of the flow to the evaporating surface difficult.

The volatile composition dispenser may include a heater 24 such as shown in FIGS. 2-4. The heater 24 may be assist in the evaporation of the volatile composition 44 from the evaporative surface 20. The heater may heat the evaporative surface through thermal conduction, convection, or induction. The heater may be in the form of a resistor, such as a chip/surface-mount resistor, through-hole, or printed resistor, for example. The heater may be in the form of a heater block having a resistor.

The heater 24 may be disposed in various locations and in various configurations. The heater may be integral with or separate from the evaporation element. Moreover, the heater may be disposed adjacent to or in contact with the evaporative surface, depending on the configuration of the evaporative surface and/or the heater.

Figure 7:
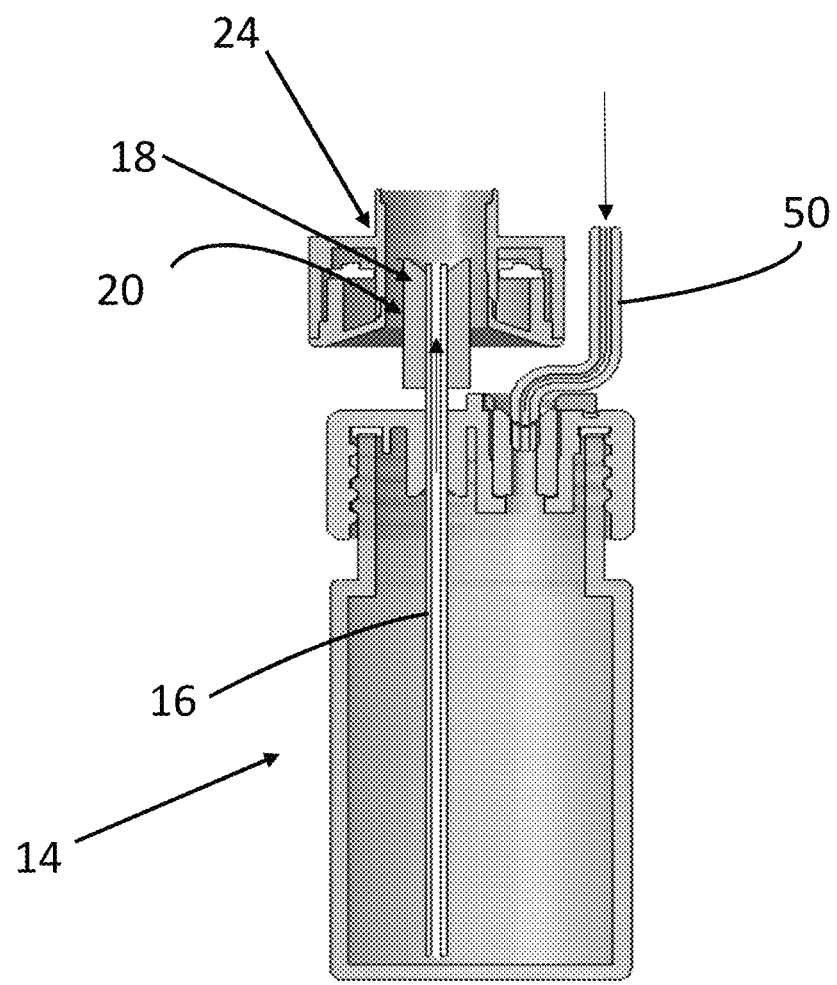
FIG. 7 is a cross-sectional view of an exemplary cartridge, evaporation member, and heater of an exemplary volatile composition dispenser.

The heater 24 may surround the evaporative surface 20 such as shown in FIG. 7. The heater 24 may be disposed above the evaporative surface 20 such as shown in FIGS. 2-4, or below the evaporative surface 20 such as shown in FIGS. 5 and 6. The heater 24 may also be disposed to one or more sides of the evaporative surface 20. The heater 4 may partially or fully surround the evaporative surface 20. The temperature of the heater may be set based upon the desired evaporation rate and/or the particular volatile composition.

The heater may be integral with the evaporation element. For example, the evaporation element may be composed at least partially of an electrically conductive material that is in electrical communication with a source of electric current. The evaporative surface or another portion of the evaporation element may comprise carbon fiber paper that can be heated upon introduction of current to the carbon fiber paper. The evaporation member may also be in the form of a hot plate.

With reference to FIGS. 1-2, the volatile composition dispenser 10 may include a fan 26. The fan 26 is configured to move a volume of air into the interior chamber 30 of the housing 12 through a housing inlet 62, around the evaporative surface 20, and out of the housing 12 through a housing outlet 64. The air flow through the housing 12 assists in dispersing the evaporated volatile composition throughout a room or area within a room. The air flow may also assist in the evaporation of the volatile composition from the evaporative surface. The fan 26 may be disposed adjacent to the evaporative surface 20. Various types of fans 26 may be used, such as centrifugal (i.e., radial) and axial fans. Suitable fans for the present disclosure include a 30×30×6 mm MagLev Motor Fan (Model MC30060V1-000U-A99), supplied by Sunon Wealth Electric Machine Industry Co., Ltd of Taiwan; and fan model RF-330TK 07800, supplied by Mabuchi Motor. Another suitable fan for the present invention may have the following specifications:
Dimension: 120×120×25 mm
Fan Speed: 800~1500 rpm+250 RPM
Max Airflow: 66.55 CFM
Max Air Pressure: 1.42 mm H20
Bearing Type: Sleeve
Operating Voltage: 5V The volatile composition dispenser includes a power source 28. The power source 28 supplies the power needed to run the electrical components of the volatile composition dispenser 10, including the air pump 22, heater 24, and fan 26, if and when present. The power source 28 may include a plug and/or cord for connecting the volatile composition dispenser to an AC/DC outlet, a battery, such as a AA battery, a AAA battery, a 9-volt battery, rechargeable battery, and/or other suitable battery. The power source may be a solar power source, such as a solar cell, for example that can receive light that can be transformed into energy to power the components of the volatile composition dispenser. FIG. 2 shows, for illustrative purposes only, an exemplary volatile composition dispenser 10 having an AC/DC plug as a power source 28. However, it is to be appreciated that a volatile composition dispenser 10 may be configured with any type of power source 28 that supplies the necessary power to run the electrical components.

As shown in FIG. 2, the volatile composition dispenser also includes a controller 62. The controller 62 controls the electrical components, such as the air pump 22, heater 24, and fan 26, when and if present in the volatile composition dispenser 10. The controller 62 may be configured as a microcontroller ("MCU") or an application specific integrated circuit ("ASIC"), for example. The controller 62 is responsible for delivering the functionality of the volatile composition dispenser, including sequence of events and timing. An exemplary controller 62 includes a Texas Instruments MSP430F2132 controller.

FIG. 7 illustrates a cross-sectional view of a portion of an exemplary volatile composition dispenser 10. As shown in FIG. 7, the evaporation member 18 may be in the form of a porous or semi-porous substrate. The heater 24 may be configured to partially or completed surround the evaporative surface 20.

The volatile composition dispenser may include one or more user input buttons or switches configured to provide an input signal to the controller when engaged by a user, such that the controller can send corresponding output signals to the electrical component. Exemplary input buttons or switches include a power on/off switch configured to power on or power off the volatile composition dispenser, an intensity button or dial configured to allow the user to adjust the amount of volatile composition dispensed by the volatile composition dispenser. As will be appreciated, the input buttons or switches can be any combination of buttons and/or switches, such as push buttons, sliders, dials, knobs, for example.

The volatile composition dispenser can comprise a sensor, such as a visible indicator, a light source, and/or an audible alert, configured to provide feedback to the user regarding the status of the volatile composition dispenser. The sensor may be used to alert the user of a property of the volatile composition dispenser. The feedback can be visual and/or audible and can indicate to the user, among other things, whether the volatile composition dispenser is powered on, what volatile composition dosing amount is being dispensed, the power level of the power source, the amount, type, or level of the volatile composition within the reservoir, and/or any other suitable feedback helpful or beneficial to the user. Various other sensors may be used, such as temperature sensors, motion sensors, and/or air quality sensors.

When present, the sensor may comprise one or more one indicators, such as a plurality of light sources, for example, electrically coupled to the controller and/or to the power source, and a translucent portion in the housing, such that the one or more indicators can be viewed by the user though the housing. If present, the one or more indicators can be oriented in any suitable fashion such that various lights of the one or more indicators can emit visible light through the translucent portion of the housing, depending on what type of feedback is being provided to the user. The translucent portion of the housing can comprise any suitable shape and the one or more indicators can be arranged in a similar shape so that as one indicator, such as a light source, for example, is powered or unpowered, the user is provided with a first feedback and, as two or more light sources are powered or unpowered, the user is provided with at least a second feedback and so forth. Any buttons or switches may also be at least partially translucent allowing for one or more indicators to be viewable through the button.

In the instance where the battery voltage or run time is viewed as the indicator of the full life of the reservoir, the controller could be programmed to provide a signal to the user such as turning on a red light or provide a flashing light to indicate that the reservoir is empty and/or the cartridge needs to be replaced.

The present disclosure also includes a method of evaporating a volatile composition into the air. With reference to FIGS. 1-4, the method may comprise the step of providing a volatile composition dispenser 10 having a reservoir 32 and an evaporation element 18 having an evaporative surface 20. The method includes pressurizing the reservoir 32 using an air pump 22 to direct a volatile composition 44 from the reservoir 32 to the evaporative surface 20. The volatile composition 44 may flow from the reservoir 32 to the evaporative surface 20 through a transport member 16 that is in fluid communication with the reservoir 32 at one end and in fluid communication with the evaporative surface 20 at the opposite end. The method also includes the step of evaporating the volatile composition 44 from the evaporative surface 20. A heater 24 may be used to assist in the evaporation of the volatile composition 44 from the evaporative surface. The method of evaporating a volatile composition may also include activating a fan 26 to direct a volume of air over or around the evaporative surface 20.

A volatile composition 44 may evaporate from the evaporative surface 20 at various evaporation rates, depending upon the desired intensity, room size, and the like.

An air pump 22 may be configured to intermittently or continuously deliver the volatile composition 44 from the reservoir 32 to the evaporative surface 20. The flow rate of volatile composition 44 from the reservoir 32 to the evaporative surface 20 can be selected based upon the desired intensity or noticeability over a particular time period and/or based upon the room size. For example, the air pump may pump a single dose of volatile composition to the evaporative surface once every so many minutes or may continuously deliver an amount of volatile composition to the evaporative surface over a period of time.

The volatile composition dispenser may also include an overflow drain that allows some fluid to flow back into the reservoir if too much fluid is dosed by the air pump to the evaporative surface at one time. A one-way valve may be used to prevent air from escaping the cartridge and/or to prevent the volatile composition from leaving out of the reservoir if the cartridge is tipped over.

When present, a heater 24 may be configured to operate continuously or intermittently. The heater 24 may be configured to turn on after a dose of volatile composition 44 is delivered to the evaporative surface 20. For example, the air pump 22 may be activated for an amount of time, such as 1 second, and subsequently the heater 24 may be turned on for a period of time to evaporate the dose of volatile composition 44 from the evaporative surface 20. If operated intermittently, the heater 24 may be turned on for a period ranging from one minute to 20 minutes, alternatively about five minutes to about 15 minutes, alternatively about 10 minutes.

When present, a fan 26 may be configured to operate continuously or intermittently. The fan 26 may be turned while the heater 24 is turned on, so that while the volatile composition 44 is being evaporated, the fan 26 is directing the evaporated volatile composition out of the volatile composition dispenser 10 and into the air. The air flow rate from the fan may be any desired flow rate, depending upon the room size, desired intensity, and the like. For example, the fan 26 may generate an air flow rate through the interior chamber 30 of the housing 12 in the range of about 3.5 m$^3$ per hour. The duration of activation of the fan 26 or the flow rate of the volume of air provided by the fan 26 can be adjusted to provide a higher or lower intensity of volatile composition evaporation and/or dispersion from the volatile composition dispenser 10. The fan 26 may toggle on and off for a duty cycle of about 5% to about 50%, or from about 8% to about 20%.

Operating the fan 26 and/or the heater 24 intermittently for a period of time substantially equal to the time required to evaporate the volatile composition 44 from the evaporate surface 20 can conserve power and/or extend the life of a power source 28 such as a battery. In addition, intermittently operating the air pump 22, heater 24 and/or fan 26 can also control the evaporation rate of volatile composition.

The volatile composition dispenser may be connectable with a communication network over Wi-Fi or ad hoc, wireless mesh network. For example, the communication network may be used to remotely control the volatile composition dispenser, including turning the volatile composition dispenser on or off or adjusting the flow rate, fan speed, or heater. The communication network may also be used to link the use of the volatile composition dispenser with the use of other appliances, lights, HVAC units, and the like.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition dispenser comprising:
   a reservoir for containing a volatile composition, the volatile composition comprising a mixture of perfume raw materials, the reservoir having an air inlet and a liquid outlet that is spaced apart from the air inlet,
   a transport member having a first end portion and an opposing second end portion, wherein the first end portion is in liquid communication with the reservoir and the second end portion extends through the liquid outlet of the reservoir,
   an evaporative surface disposed outside of the reservoir and proximal to the second end portion of the transport member, wherein the volatile composition is received onto the evaporative surface from the second end portion of the transport member, and wherein the volatile composition evaporates into the air from the evaporative surface; and
   an air pump in gaseous communication with the air inlet of the reservoir, wherein the air pump is configured to pressurize the reservoir and force the volatile composition from the reservoir, through the transport member, and to the evaporative surface.

2. The dispenser of claim 1 further comprising a heater in communication with the evaporative surface.

3. The dispenser of claim 1 further comprising a fan disposed adjacent to the evaporative surface.

4. The dispenser of claim 1 further comprising a cartridge and a housing, the cartridge comprising the reservoir and transport member, and wherein the cartridge is releasably connectable with the housing.

5. The dispenser of claim 4, wherein the evaporative surface is connected with the cartridge.

6. The dispenser of claim 5, wherein the evaporative surface comprises a material selected from the group consisting of metal, plastic, glass, and combinations thereof.

7. The dispenser of claim 1, wherein the evaporative surface is air permeable.

8. The dispenser of claim 1 further comprising a controller in electrical communication with the air pump, and a power source that is in electrical communication with the air pump and controller.

9. The dispenser of claim 1, wherein the transport member further comprises a restriction member disposed in the second end portion.

10. A volatile composition dispenser comprising:
a housing;
a cartridge that is releasably connectable with the housing, the cartridge comprising a reservoir and a transport member, wherein the reservoir is configured to contain a volatile composition, the volatile composition comprising a mixture of perfume raw materials, the reservoir having an air inlet and a liquid outlet that is spaced apart from the air inlet, and wherein the transport member has a first end portion and an opposing second end portion, wherein the first end portion is in liquid communication with the reservoir and the second end portion extends through the liquid outlet of the reservoir;
an evaporation member disposed outside of the reservoir and proximal to the second end portion of the transport member, the evaporation member having an evaporative surface, wherein the evaporation member is selected from the group consisting of: a bowl, a plate, a porous substrate, a semi-porous substrate, and combinations thereof, wherein the volatile composition is received onto the evaporative surface from the second end portion of the transport member, and wherein the volatile composition evaporates into the air from the evaporative surface;
an air pump in gaseous communication with the air inlet of the reservoir, wherein the air pump is configured to pressurize the reservoir and force the volatile composition from the reservoir, through the transport member, and to the evaporative surface; and
a power source.

11. The dispenser of claim 10 further comprising a heater in communication with the evaporative surface.

12. The dispenser of claim 10 further comprising a fan disposed adjacent to the evaporative surface.

13. The dispenser of claim 10 further comprising a controller in electrical communication with the air pump and the power source.

* * * * *